(12) United States Patent
Spadafora et al.

(10) Patent No.: US 12,134,756 B2
(45) Date of Patent: Nov. 5, 2024

(54) MODULAR KIT FOR INTEGRATION AND INSTALLATION OF ONE OR MORE BIOREACTORS FOR MICROALGAE CULTIVATION

(71) Applicant: Politecnico Di Milano, Milan (IT)

(72) Inventors: Saverio Pasquale Spadafora, Milan (IT); Ingrid Paoletti, Milan (IT)

(73) Assignee: Politecnico Di Milano, Milan (IT)

( * ) Notice: Subject to any disclaimer, the term of this patent is extended or adjusted under 35 U.S.C. 154(b) by 769 days.

(21) Appl. No.: 17/426,778

(22) PCT Filed: Feb. 24, 2020

(86) PCT No.: PCT/IB2020/051524
§ 371 (c)(1),
(2) Date: Jul. 29, 2021

(87) PCT Pub. No.: WO2020/174351
PCT Pub. Date: Sep. 3, 2020

(65) Prior Publication Data
US 2022/0098533 A1    Mar. 31, 2022

(30) Foreign Application Priority Data
Feb. 25, 2019  (IT) .......................... 102019000002641

(51) Int. Cl.
*C12M 1/00* (2006.01)
*C12M 1/12* (2006.01)
(Continued)

(52) U.S. Cl.
CPC ............ *C12M 21/02* (2013.01); *C12M 23/06* (2013.01); *C12M 23/22* (2013.01); *C12M 23/44* (2013.01); *C12M 23/48* (2013.01); *C12M 31/02* (2013.01)

(58) Field of Classification Search
None
See application file for complete search history.

(56) References Cited

U.S. PATENT DOCUMENTS

2010/0105125 A1    4/2010    Haley, III

FOREIGN PATENT DOCUMENTS

| CN | 101935610 B | 5/2013 |
| CN | 104611191 A | 5/2015 |

(Continued)

OTHER PUBLICATIONS

International Search Report and Written Opinion dated May 24, 2020, issued in PCT Application No. PCT/IB2020/051524, filed Feb. 24, 2020.

*Primary Examiner* — Neil N Turk
(74) *Attorney, Agent, or Firm* — Workman Nydegger

(57) ABSTRACT

A modular kit for integration and installation of one or more bioreactors for microalgae cultivation includes: —at least one bioreactor for microalgae cultivation, in the form of a vertically arranged transparent tubular column; —a supporting structure adapted to integrate and support the base of the at least one bioreactor, and also adapted to internally house a first connection to a system for loading and unloading a cultivation vector fluid into/from the at least one bioreactor, and a second connection to a system for supplying CO2-supplemented air into the at least one bioreactor; —multiple modules forming respective frames with internal empty spaces and adapted to be connected to one another to house, in the empty spaces, the at least one bioreactor; the multiple modules being also so shaped as to convey filtered light into the at least one bioreactor.

5 Claims, 6 Drawing Sheets

(51) Int. Cl.
*C12M 3/00* (2006.01)
*F24S 23/00* (2018.01)
*F24S 23/70* (2018.01)

(56) References Cited

FOREIGN PATENT DOCUMENTS

| | | | | |
|---|---|---|---|---|
| CN | 104651227 | A | 5/2015 | |
| CN | 107779384 | A | 3/2018 | |
| CN | 108359580 | A | 8/2018 | |
| EP | 4394024 | A1 * | 7/2024 | ............. B01D 53/84 |
| WO | WO-2010132812 | A2 * | 11/2010 | ............ C12M 21/02 |

* cited by examiner

MODULAR KIT FOR INTEGRATION AND INSTALLATION OF ONE OR MORE BIOREACTORS FOR MICROALGAE CULTIVATION

FIELD OF THE INVENTION

The present invention relates to a modular kit for integration and installation of one or more bioreactors for microalgae cultivation.

BACKGROUND ART

Techniques which can be used for microalgae cultivation in large industrial systems only, whether in open or protected environments are known. Also, systems for integrating the systems in environments other than those exclusively used for cultivation, in association with large-scale building organisms or similar structures and with hard-to-manage, complex installations are known.

Such engineering and architectural systems can be hardly integrated into a domestic environment, and do not meet the requirement of space delimitation by means of a filtering wall. The latter comprises, in a known manner, a framework of elements through which a grid is formed which can filter light, vision and sound, and also control the air flow.

A need is therefore felt for creating an easily assemblable system for a broader user base, which can promote the spread of small microalgae systems in domestic environments, thus meeting a new demand not tackled by other solutions.

SUMMARY OF THE INVENTION

It is therefore the object of the present invention to propose a modular kit for integration and installation of one or more bioreactors for microalgae cultivation, which is aimed at overcoming the above-mentioned drawbacks.

The solution involves conceiving, designing and building a kit for domestic use, containing a bioreactor system for microalgae cultivation.

The present invention concerns a modular kit for integration and installation of one or more bioreactors for microalgae cultivation, said kit comprising:

- at least one bioreactor for microalgae cultivation, in the form of a vertically arranged transparent tubular column;
- a supporting structure adapted to integrate and support the base of said at least one bioreactor, and also adapted to internally house a first connection to a system for loading and unloading a cultivation vector fluid into/from said at least one bioreactor, and a second connection to a system for supplying CO2-supplemented air into said at least one bioreactor;
- multiple modules forming respective frames with internal empty spaces and adapted to be connected to one another to house, in said empty spaces, said at least one bioreactor; said multiple modules being also shaped so as to convey filtered light into said at least one bioreactor.

The present invention also concerns a bioreactor for microalgae cultivation, suitable for insertion into the modular kit.

It is a particular object of the present invention to provide a modular kit for integration and installation of one or more bioreactors for microalgae cultivation as will be further set out in the claims, which are an integral part of the present description.

BRIEF DESCRIPTION OF THE DRAWINGS

Further objects and advantages of the present invention will become apparent from the following detailed description of a preferred embodiment (and variants) thereof and from the annexed drawings, which are supplied merely by way of non-limiting example, wherein.

In the drawings, the same reference numerals identify the same items or components.

DETAILED DESCRIPTION OF SOME EMBODIMENTS OF THE INVENTION

Figure 1:
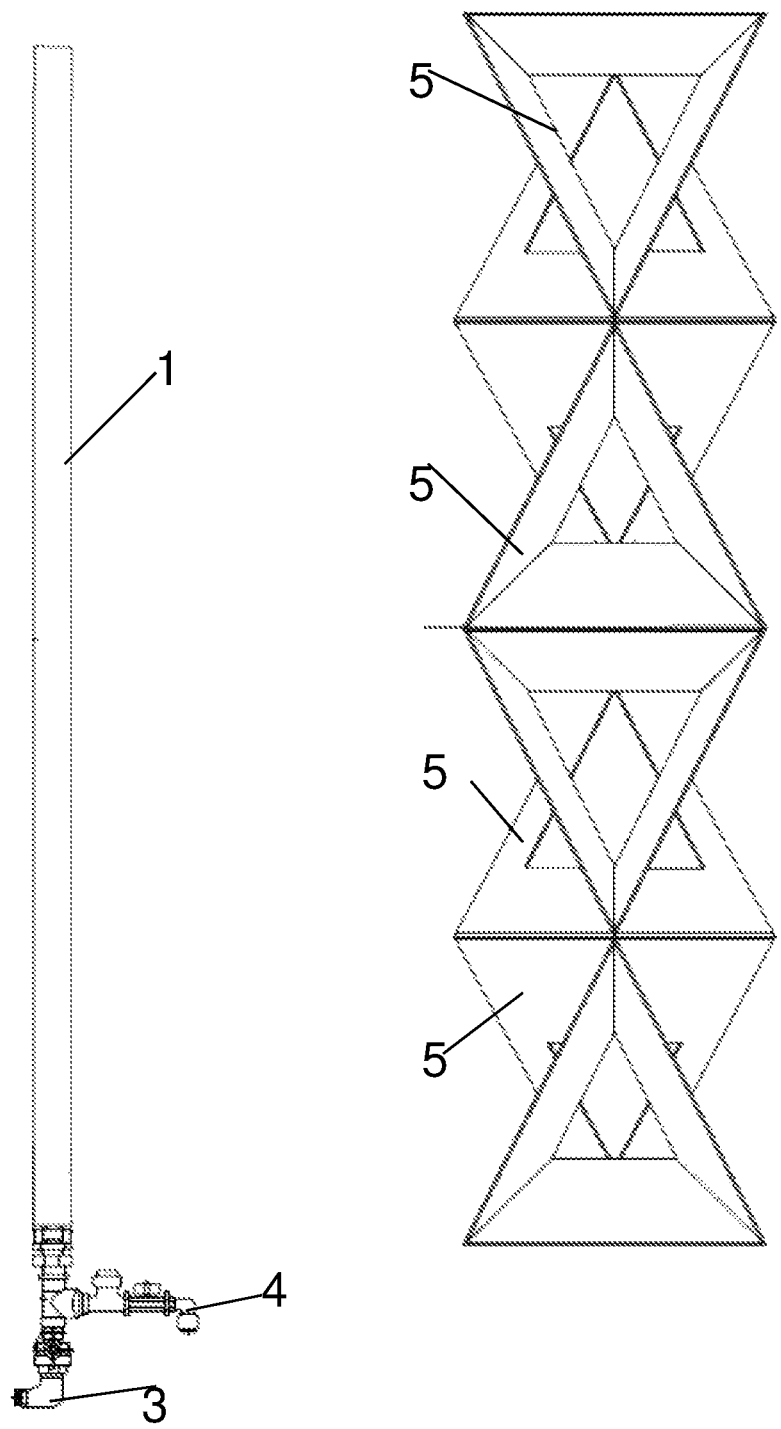
FIG. 1 shows an example of embodiment of a bioreactor column for microalgae cultivation and an assembly of modules included in the kit of the invention.
Figure 2:
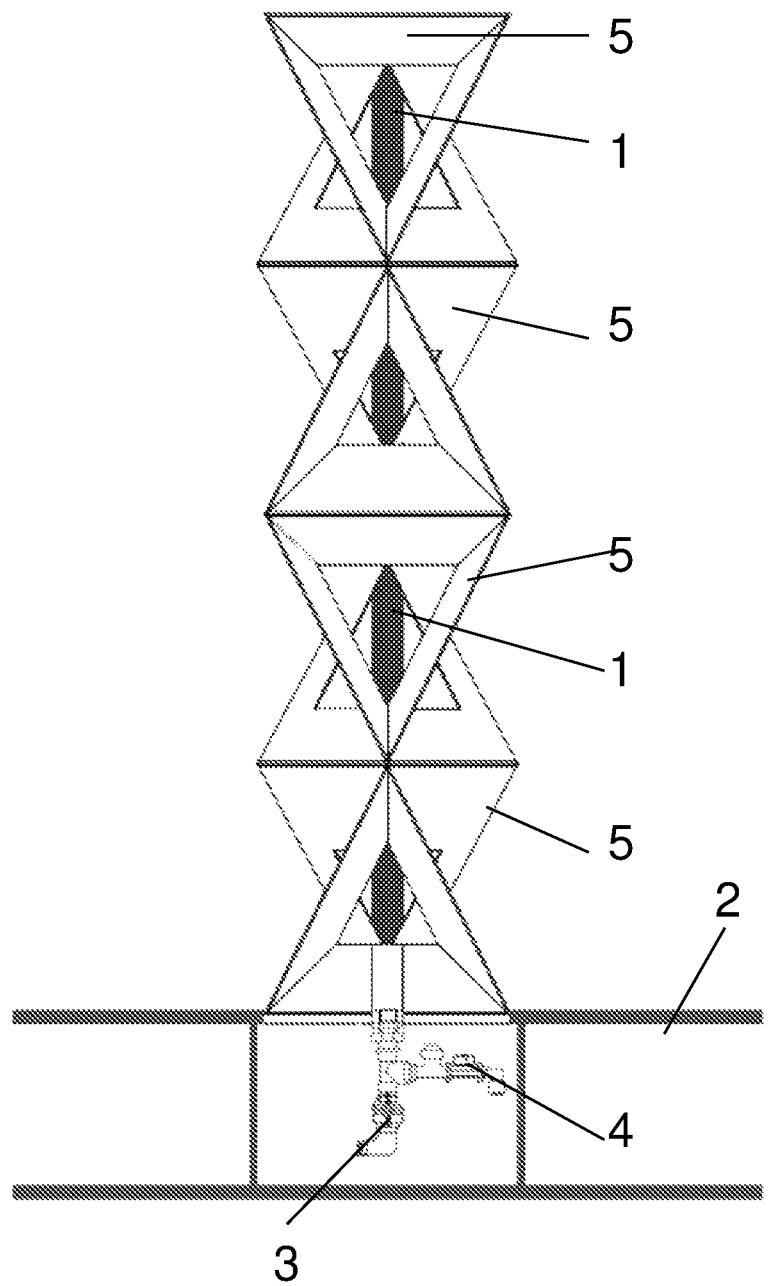
FIG. 2 shows an example of the assembling of the modules and the column of the kit of the invention.
Figure 3:
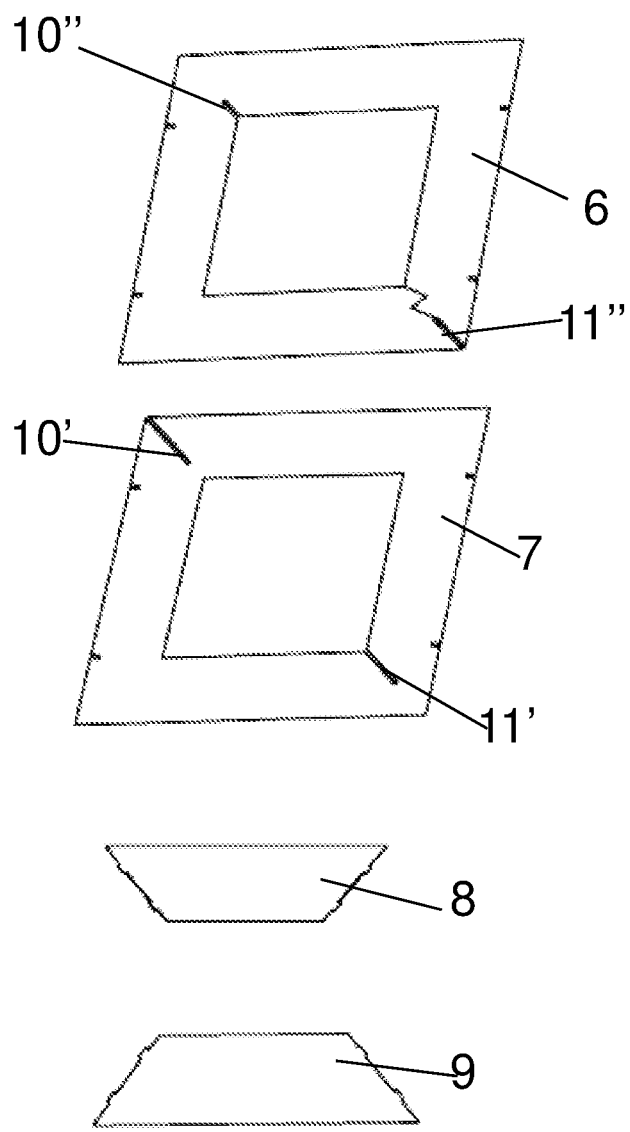
FIG. 3 shows the constituent elements of a module.

The following will describe an example of embodiment of a bioreactor for microalgae cultivation in the form of a modular kit.

The kit includes an integrated system consisting of a modular structure formed by assemblable elements that extends horizontally and vertically, and an integrated installation consisting of bioreactors for microalgae cultivation controlled via a parallel connection.

From an architectural viewpoint, the kit provides a filtering wall for space delimitation. Due to the framework of elements, a grid is formed which can filter light, vision and sound, and also control the air flow. The kit can be adapted to different development shapes, i.e. both horizontally, whether along curvilinear or straight directions, and vertically, in order to generate an organism capable of adapting itself to indoor or outdoor environments and fulfilling specific requirements.

Moreover, since this is an active structure for microalgae cultivation, it comprises transparent tubular elements that make up the bioreactors, a system for loading and unloading cultivation vector fluid, integrated with a system for supplying CO2-supplemented air, and an illumination control system, which is essential for microalgae growth, characterized by a geometry of constituent modules adapted to generate a natural or electric light condensing effect on the bioreactor.

More specifically, with reference to the drawings, a transparent tubular column 1, constituting a bioreactor, is arranged vertically on a supporting structure 2 which integrates and supports the column base, and which permits the serial and/or parallel arrangement of multiple vertical columns, meaning that the columns can be arranged either along one line or along multiple side-by-side lines.

The microalgae development principle is per se known. This type of bioreactor has a number of innovative aspects. It comprises a vertical tubular element, fitted at the bottom with an installation conceived for easily controlling the loading/unloading of cultivation vector fluid and the intake of CO2-charged ambient air. At the top, the tubular element is open or protected by a wire cap, so that the oxygen produced by photosynthesis is released into the environment. One of the main objects of microalgae cultivation is $CO_2$ abatement, because the bioreactor becomes a $CO_2$ filter.

At the basis of each column there is a connection 3 to a system for loading and unloading the cultivation vector fluid from/into the column, and a connection 4 to a system for supplying $CO_2$-charged air into the column.

A system for controlling the illumination of the geometry of constituent modules 5 is applied to each column.

A module 5 comprises two lozenge-shaped elements 6, 7 in the form of an internally empty frame, and two trapezoid elements 8, 9. The internal empty space of the lozenge-shaped elements permits the insertion of the column. The lozenge-shaped elements 6, 7 have slots on their sides 10', 11' (lozenge 6), 10", 11" (lozenge 7) that enable them to be joined to each other, so that they turn out to be perpendicular to each other. The slot 10' fits into the slot 10", and the slot 11' fits into the slot 11".

The two trapezoid elements 8, 9 are fitted at the two opposite ends of the jointed lozenges by means of tabs they are equipped with, and are secured with suitable glue or another system, depending on the material in use, so as to make the module firm and stable.

Figure 4:
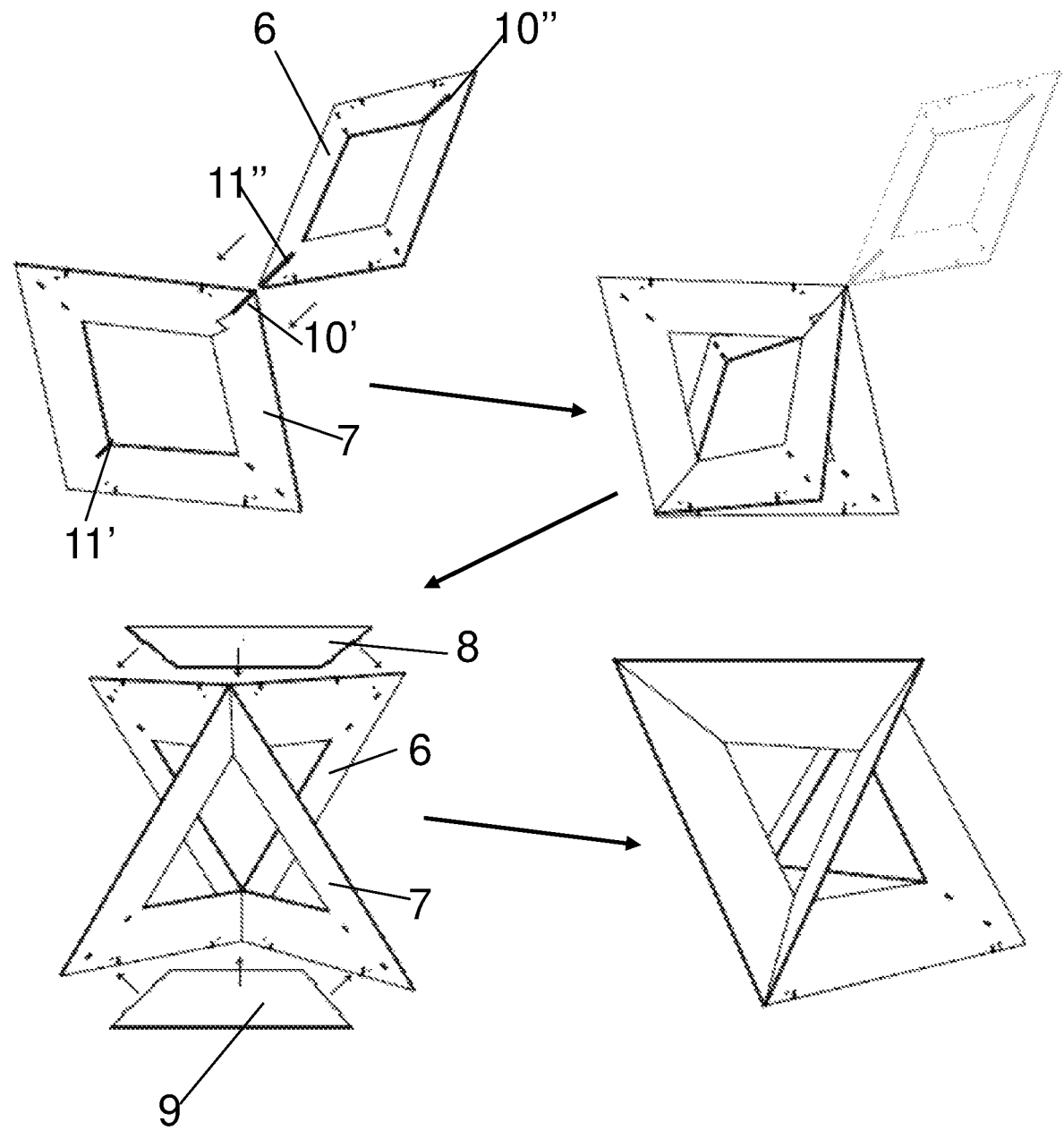
FIGS. 4 and 5 show the modes of assembling one module and multiple modules, respectively.

The arrows in FIG. 4 indicate the steps required for assembling a module.

Figure 5:
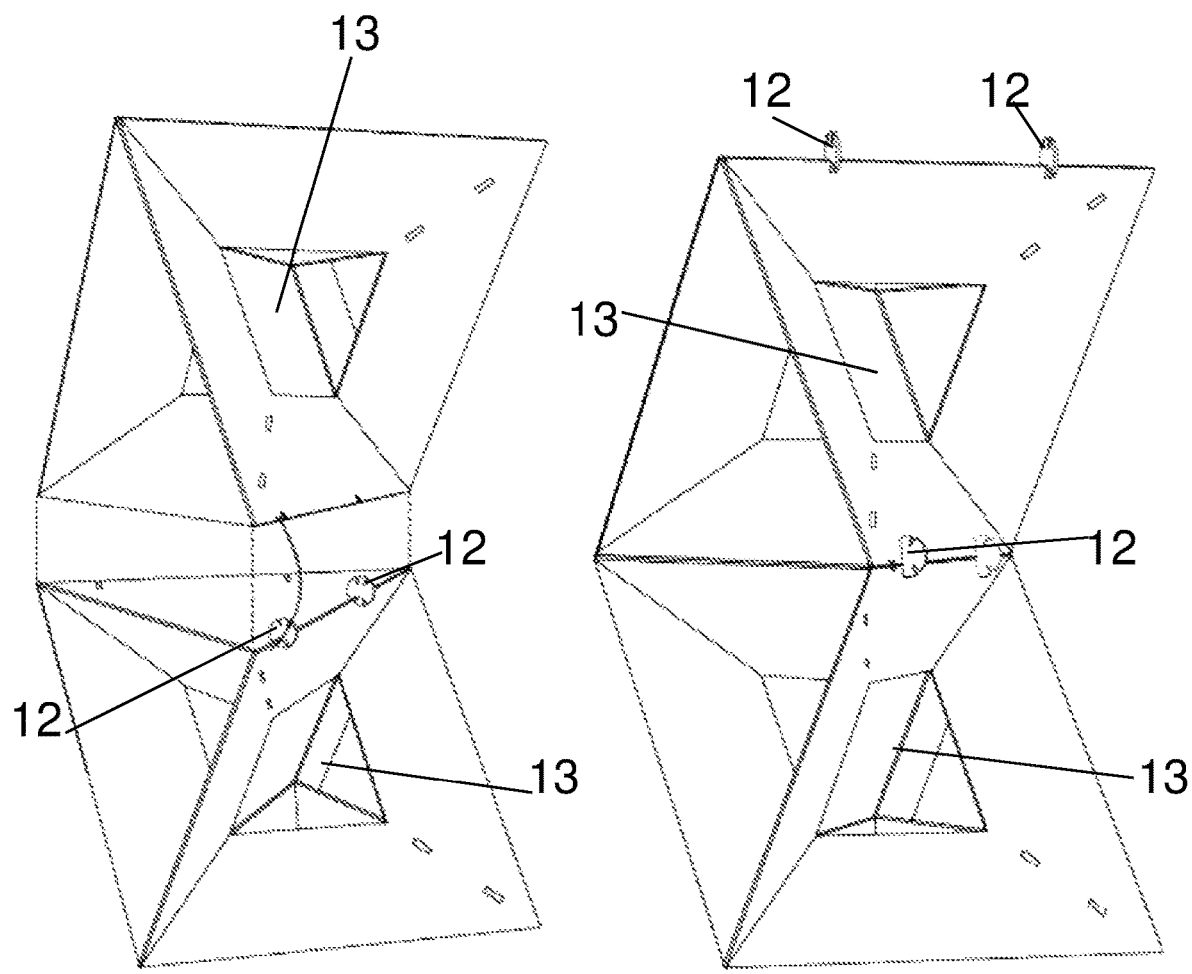

With reference to FIG. 5, the modules can be connected to one another by means of connection disks 12 applied to additional slots on the edges of the lozenge-shaped elements. Therefore, the modules can be either arranged side by side horizontally or stacked vertically.

The modules form superimposed internal empty spaces 13, such that they can internally house a column bioreactor. A structure of stacked modules arranged side by side can thus be created, which can house, in its internal empty spaces, parallel side-by-side columns following a straight or curved line. It is also possible to create a three-dimensional structure of stacked modules arranged side by side, so that parallel columns arranged in a matrix pattern can be housed in its empty spaces.

Figure 6:
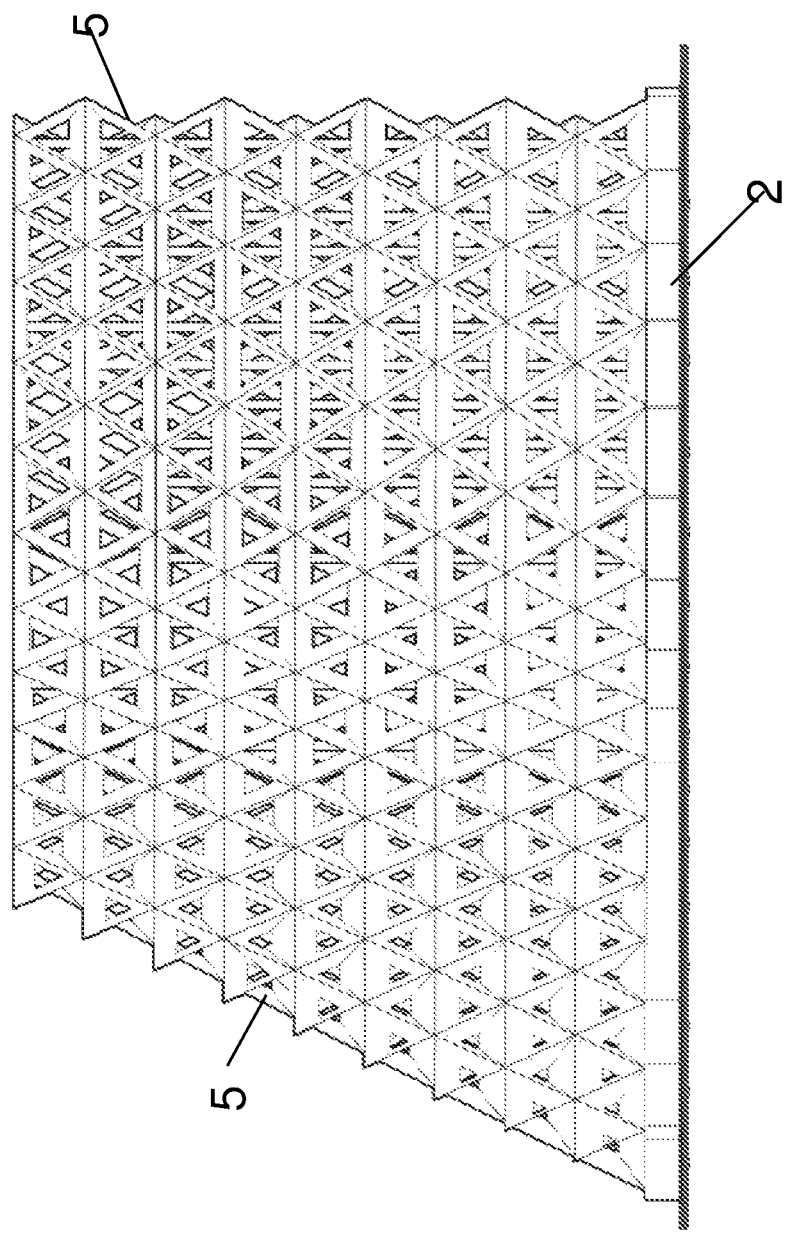
FIG. 6 shows an example of spatial arrangement of the kit.

FIG. 6 shows an example of spatial arrangement of the resulting structure.

The effect of conveying light towards the bioreactor, generated by the module's geometry, is a parameter that can be controlled to advantage in poor lighting conditions. The inner cavity of the module changes with the width of the solid faces of the same. This permit changing the light conveyance capacity as well as the ventilation capacity. These aspects are important for controlling the environments of the two zones delimited by the filtering wall; hence, they are important not only for optimizing the microalgae culture conditions, but also for creating a control architecture between the outside and the inside of the wall.

In order to control all the generative parameters of the variable basic module, three-dimensional development CAD software can be used.

The operational test was carried out on a prototype conceived for indoor or outdoor installation, and gave very satisfactory results from both the architectural and the engineering viewpoints.

The module can be made up, for example, of opal methacrylate plates having a diversified transparency gradient. In this way, it is possible to control colour saturation, and hence transparency. The four constituent elements of the module can be obtained from the plates by numerical-control laser cutting according to two-dimensional geometries obtained from the three-dimensional geometry and generated by the prototype shape control algorithm.

The protected microalgae cultivation environment (column bioreactor 2) can be built from a tube of transparent methacrylate.

The above-described example of embodiment may be subject to variations without departing from the protection scope of the present invention, including all equivalent designs known to a man skilled in the art.

The elements and features shown in the various preferred embodiments may be combined together without however departing from the protection scope of the present invention.

From the above description, those skilled in the art will be able to produce the object of the invention without introducing any further construction details.

The invention claimed is:

1. A modular kit for integration and installation of one or more bioreactors for microalgae cultivation, said kit comprising:
   at least one bioreactor for microalgae cultivation, in the form of a vertically arranged transparent tubular column;
   a supporting structure adapted to integrate and support the base of said at least one bioreactor, and also adapted to internally house a first connection to a system for loading and unloading a cultivation vector fluid into/from said at least one bioreactor, and a second connection to a system for supplying $CO_2$-supplemented air into said at least one bioreactor,
   multiple modules forming respective frames with internal empty spaces and adapted to be connected to one another to house, in said empty spaces, said at least one bioreactor; said multiple modules being also shaped so as to convey light into said at least one bioreactor,
   wherein each one of said modules comprises:
      two lozenge-shaped elements in the form of internally empty frames, and two trapezoid elements;
      said two lozenge-shaped elements being connected to each other perpendicularly, so as to form said internal empty space;
      said two trapezoid elements being located at two opposite ends of said two lozenge-shaped elements connected to each other.

2. The modular kit according to claim 1, wherein said lozenge-shaped elements have slots at the edges adapted to allow for a join connection between said two lozenge-shaped elements.

3. The modular kit according to claim 1, wherein said multiple modules are connected together side-by-side and/or stacked in a one-dimensional or two-dimensional manner, being able to house in said respective internal empty spaces multiple parallel bioreactors arranged side-by-side in a column along a straight or curved line, or in multiple parallel columns arranged in a matrix.

4. The modular kit according to claim 1, wherein said multiple modules are made up of opal methacrylate plates having a diversified transparency gradient, in order to control colour saturation and transparency.

5. The modular kit according to claim 1, wherein said transparent tubular column of the bioreactor is open or comprises a wire cap in its top part, so that the oxygen produced by photosynthesis during the microalgae cultivation process is released into the environment, and $CO_2$ emission is reduced.

\* \* \* \* \*